United States Patent
Duran Toro et al.

(10) Patent No.: US 9,394,786 B2
(45) Date of Patent: Jul. 19, 2016

(54) METHOD AND SYSTEM FOR IN SITU, CONTINUOUS AND REAL-TIME ANALYSIS OF MINERAL CONTENT IN DRILLING DEBRIS

(71) Applicant: INGENIEROS MATEMÁTICOS CONSULTORES ASOCIADOS S.A., Santiago (CL)

(72) Inventors: Mario Manuel Duran Toro, Santiago (CL); Ricardo Oliver Hein Hoernig, Santiago (CL); Pedro Ramaciotti Morales, Santiago (CL); Pedro Antonio Escárate Monetta, Santiago (CL)

(73) Assignee: INGENIEROS MATEMATICOS CONSULTORES ASOCIADOS S.A. (CL)

( * ) Notice: Subject to any disclaimer, the term of this patent is extended or adjusted under 35 U.S.C. 154(b) by 0 days.

(21) Appl. No.: 14/476,480

(22) Filed: Sep. 3, 2014

(65) Prior Publication Data

US 2015/0068806 A1    Mar. 12, 2015

Related U.S. Application Data

(60) Provisional application No. 61/874,541, filed on Sep. 6, 2013.

(51) Int. Cl.
*E21B 49/00* (2006.01)
*E21B 49/02* (2006.01)

(52) U.S. Cl.
CPC .............. *E21B 49/00* (2013.01); *E21B 49/003* (2013.01); *E21B 49/005* (2013.01); *E21B 49/02* (2013.01)

(58) Field of Classification Search
CPC ......... E21B 49/02; E21B 49/005; E02D 1/00; G01N 33/24; G01N 2021/8592
See application file for complete search history.

(56) References Cited

U.S. PATENT DOCUMENTS

| | | | |
|---|---|---|---|
| 3,980,882 A | 9/1976 | Carr-Brion et al. | |
| 5,241,178 A * | 8/1993 | Shields | G01N 21/359 250/339.02 |
| 6,100,526 A * | 8/2000 | Mayes | A01D 41/127 250/339.11 |
| 7,667,838 B2 * | 2/2010 | Ackerman | B01F 5/0619 356/246 |
| 9,000,319 B2 * | 4/2015 | Deefholts | B07C 5/342 209/576 |
| 2004/0239926 A1 * | 12/2004 | Sokolowski | G01J 3/42 356/319 |
| 2010/0278302 A1 | 11/2010 | Yokoyama et al. | |
| 2011/0260073 A1 * | 10/2011 | Duran Toro | G01N 1/2202 250/373 |
| 2012/0171338 A1 * | 7/2012 | Hamid | G01N 21/85 426/231 |
| 2015/0008162 A1 * | 1/2015 | Cadieux, Jr. | A24B 15/10 209/3.3 |

FOREIGN PATENT DOCUMENTS

| WO | WO 95/09962 A1 | 4/1995 |
|---|---|---|
| WO | WO 2010/052645 A1 | 5/2010 |

* cited by examiner

*Primary Examiner* — Kara E Geisel
*Assistant Examiner* — Shawn Decenzo
(74) *Attorney, Agent, or Firm* — Merchant & Gould P.C.

(57) ABSTRACT

A method and a system for in situ measuring and analyzing, in a continuous, non-intrusive manner in real-time, one or more compounds, typically minerals present in debris from drilling or some similar material, in powder, comminuted solids or slurry form is disclosed. The method and system provide real-time, non-intrusive, continuous in situ determination of the grade of valuable minerals present in drilling pits debris generated during excavation, with a relatively low measurement error.

39 Claims, 3 Drawing Sheets

METHOD AND SYSTEM FOR IN SITU, CONTINUOUS AND REAL-TIME ANALYSIS OF MINERAL CONTENT IN DRILLING DEBRIS

This application claims benefit of U.S. Provisional Ser. No. 61/874,541, filed 6 Sep. 2013 and which application is incorporated herein by reference. To the extent appropriate, a claim of priority is made to the above disclosed application.

FIELD OF INVENTION

The present invention is related, primarily but not exclusively, to the geological and mining industry, particularly with regard to the extraction and processing of minerals, and consists of a method and a system for in situ measuring and analyzing, in a continuous, non-intrusive manner in real-time, one or more compounds, typically minerals present in debris from drilling or some similar material, in powder, comminuted solids or slurry form. The main application includes real-time, non-intrusive, continuous in situ determination of the grade of valuable minerals, such as copper, iron, silver, gold, platinum, nickel, cobalt, chromium, vanadium, manganese, molybdenum, zinc, titanium and uranium, among others, present in the drilling pits debris generated during the excavation, with a relatively low measurement error.

BACKGROUND

To determine the concentration of minerals of interest, the methods commonly used in the prior art consider the analysis of debris samples generated in the drilling of pits performed on a field whose feasibility of exploitation is to be determined. Analysis of debris or dust produced in drilling is performed, upon selection of samples, either on the drilling site or laboratory. The methods known in prior art for analysis of valuable materials concentration use different properties of the materials of interest to determine its presence and to what extent they are present.

Debris generated in a pit under excavation generally is extracted manually or mechanically, often intrusively, and taken to laboratories where is analyzed to determine its grade using chemical tests or similar.

International Patent Application WO95/09.962 is known from the prior art and discloses a system for capturing samples of the material excavated from a pit. A container that can be lowered into the pit on a cable and captures samples once inside is disclosed. After the capture, the samples can be raised to be analyzed. As usual in the prior art, the samples should be handled and transported to a laboratory for analysis and determine the degree of mineral concentration. The disadvantages of this method are: requires the drilling of the entire pit or at least part thereof, after which drilling must be stopped to remove the samples; while removing and handling samples, they become contaminated during the rise of the element that captures, generating measurement error; and cause samples must be sent to a laboratory, the response is slow, in the order of several hours, which means that when the results are available, the drilling machine is already operating elsewhere, generating two types of errors; type one error, continue drilling wherein the material is sterile, or type two error, stop drilling a place which contains valuable or commercially important minerals.

International patent WO2010/052.645 is also known from the prior art and discloses a method and a system of collection and analysis for in situ determination of concentrations of minerals in granular material originating from a shaft under excavation, in a continuous, non-intrusive manner in real-time. According to the present invention granular material collected passes to a granular material collector, subsequently entering a reading module which determines the concentration of different materials by atomic absorption spectroscopic methods operating at certain wavelengths in the visible and infrared spectrum. The collection of granular material comes from drilling dust goes up a bit of a hole digging. The concentration data of different minerals in the granular material being analysed at a given moment may be processed and transmitted to establish and/or correct logistic and operational procedures. The disadvantages of the technology disclosed in this patent application are: working with fine particulate material with humidity less than 6%, thus requiring a drying system; besides, in order to quantify the absorption of electromagnetic radiation, this technology requires a reference material. The patent application WO2010/052.645 further requires that incident radiation passes through the sample at specific wavelengths of visible and infrared spectrum between 0.2 and 22 μm to determine the mineral grade; this technology is also limited in that is not possible passing through samples of more than 2 mm in thickness, that is, can only read a thin film of material. Moreover, the range of molecular spectroscopy of patent application WO2010/052.645, whose incident radiation operates in the range of 0.2 to 22 μm, does not allow to excite all molecules and mineral compounds, among them many that also contain copper, which generates a measurement error, and it is possible to report a zero copper grade when the actual grade is greater than zero, a result of not being able to detect these compounds and molecules. Additionally, the reading means specified in the patent application WO2010/052645 uses photo-detectors, avalanche photo-diodes or photo-transistors, or charge coupled device (CCD sensors), which are very sensitive to temperature and its variations, which also generates measurement error of the grade.

Another prior art document U.S. Pat. No. 3,980,882(A) proposes an apparatus for analyzing flowable substances such as slurries using techniques such as X-ray fluorescence, infrared reflectance or emisson spectrography. The material to be analyzed is caused to flow over a plate in a very thin film so that a quantitative measurement of the elements of interest in the material can be made by analytical systems. The invention comprises an apparatus for use in the analytical determination of a given substance in a flowing material, said apparatus comprising: a member having an upwardly facing substantially planar surface; means for causing a stream of said material to flow in a substantially invariant manner over said surface in the form of a thin film; and an analytical system comprising means selectively responsive to electromagnetic radiation of at least one wavelength which corresponds to a spectral characteristic of said given substance, said selectively responsive means being disposed in fixed relationship to said surface out of contact with said film for receiving radiation travelling from the vicinity of a given portion of said film. The disadvantages of the technology disclosed in this patent are that the material should flow over a plate in a substantially invariant manner in the form of a thin film, making impossible to analyze well flows containing solid particles, since these introduce variability in the film thickness and tends to scatter spreading by gravity on an inclined plane; the technology does not work well with fine powders, which contain the highest concentrations of valuable minerals and tend to be more volatile, which may damage the analytical system in the presented configuration or escape to their measurement; the need to operate with a thin film prevents passing larger flows against the analytical system, or, if required, would be necessary to cover an area of large extent.

The U.S. patent application US20100278302 (A1) is known from the prior art and discloses a specific element detecting apparatus for detecting the presence or absence of a specific element or the concentration of the specific element in a measurement target, characterized by providing transporting means that transports the measurement target, providing fluorescent X-ray measuring device that radiates an X-ray to the measurement target and measures a fluorescent X-ray generated thereby to detect the presence or the content concentration of the specific element, above midstream of a transporting path of the transporting means, inserting a resin film between a measuring window of the fluorescent X-ray measuring device, through which the fluorescent X-ray is introduced, and the measurement target on the transporting means, and feeding a clear part of the fresh resin film between the measuring window and the measurement target along with repetition of detection of the specific element. The disadvantage of this apparatus is that the unconfined horizontal transport of the target material to be measured by conveyor belts or other similar means does not prevent the loss of finer and volatile particles, which contain higher concentrations of valuable minerals.

In many production processes related to the extraction and processing of materials or substances of interest from certain sets of raw materials is essential to know quickly and accurately the concentration or content of certain compounds present in said raw materials. In the case of mining is necessary to know the concentration of one or more valuable minerals, subject to be extracted and processed from a given ore body, to determine the commercial feasibility of its extraction and to optimize its extraction and post-processing. Therefore for determining the mineral content present in the debris of prospective drilling there is need to reduce existent inefficiencies, errors caused by biased sampling, incapacity to take samples from all drilling pits at all depths in a reasonable time and alteration of samples associated with the loss of valuable fine material or contamination with particles suspended in the environment, which causes measurement error.

SUMMARY

To solve the technical problem abovementioned it has been designed and developed a technology that integrates the efficient collection, proper conditioning and real-time, non-intrusive, continuous analysis of debris produced during a drilling, at the excavation site and with relatively low measurement error.

The present invention consists of a method and a collection and analysis system for the in situ determination of concentrations of one or more minerals in debris from prospective drillings, in a continuous, non-intrusive manner in real-time. According to the present invention, debris is collected by a collector, is adapted into a conditioning module and is then entered into a reading module, wherein the concentration of one or more minerals by means of spectroscopic methods is determined. The debris, either as a dry, moist granular material or as a slurry, typically coming from granular material goes up through the bit of a drill excavating a drilling pit. The information of mineral content in the debris being analyzed can be processed and transmitted remotely to establish, control or modify logistics and operational procedures.

The system and method of the present invention measure absorption, reemission or diffraction of photons from a portion of the debris by spectroscopic techniques in certain ranges of wavelengths of the electromagnetic spectrum, then relate this data to concentrations using calibrations performed to compare with measurements made by traditional methods. It is more flexible, less expensive and, above all, faster, especially to obtain results, than the methods, apparatus and traditional systems from prior art. Being fast and easy, for example, allow you to decide when using the method and system of the present invention whether to stop an ongoing excavation when the pit is considered barren of their mineral content. Its measurement error is less than ±2% over 10% ore grade and is less than ±0.1% between 0% and 10% ore grade.

The system and method of the present invention collects, conditions and evacuates debris automatically, without requiring the intervention of an external operator operating in situ, and functions in an absolutely continuous way. With regard to prior art techniques, downtime during the operation is prevented, transporting samples to remote analysis locations is prevented and the requirement of personnel involved in this process is decreased.

In the present invention, the upward transport of debris with an incident angle of 15° to 90° from the horizontal by spectroscopic reading area by upward transportation media such as a screw conveyor, enables compacting debris by gravity and therefore greater accuracy and homogeneity in the measurement than in prior art systems. This transport system allows a fully continuous operation and prevents recirculation of material against reading spectroscopic means.

In the present invention, the use of ducts, chambers and hermetically sealed modules, either with or without the presence of vacuum or positive pressure, allows debris adjustment for analysis with minimal intervention, adulteration and loss, maintaining the debris confined in the system between collection and exit, except for an optional evacuation duct in the conditioning module, which removes excess material.

In the present invention the eventual use of various spectroscopic techniques simultaneously allows to obtain various real-time information on analyzed compounds of interest, taking advantage of the inherent advantages of each technique, allowing a more flexible operation than prior art techniques.

Along with measuring the concentration in real-time, the depth of an excavation of a pit to be analyzed can be recorded, to associate a concentration to each depth. It is for this reason that the present invention allows to continuously analyze the debris excavated from a pit and generate a continuous profile of the concentration of a particular mineral in terms of pit depth.

This continuous mineral concentration profile is more accurate since contamination and handling of the extracted debris from pits is prevented; so more accurate information associated with great precision to drill site is obtained, it saves time in the analysis allowing to obtain valuable information about concentration of all kinds of minerals in relation with the depth profile; consequently, the important, costly and irreversible decisions about the blasting of rocks and on how to process the ore are more successful.

In the prior art important part of the excavated material being more volatile escapes from analysis processes. In copper mining, for example, where you want to estimate the percentage of copper in the soil, particles containing higher concentration of this mineral are smaller and therefore more likely to get lost in the manipulation or election of a part of the dust cloud generated when drilling a pit. The results of the study conducted by Dr. Marcos Alfaro and showed in "Introducción al Muestreo Minero" performed for the Institute of Mining Engineers of Chile (Instituto de Ingenieros de Minas de Chile), Santiago de Chile, 2002, shows the relationship between the size of the particles extracted in excavating a pit and the copper content of these for a sample. The present invention includes a system and method that prevents the loss of fine particulate material of debris so more accurate values for the concentrations of minerals in the pits being excavated are obtained.

DETAILED DESCRIPTION

Figure 1:
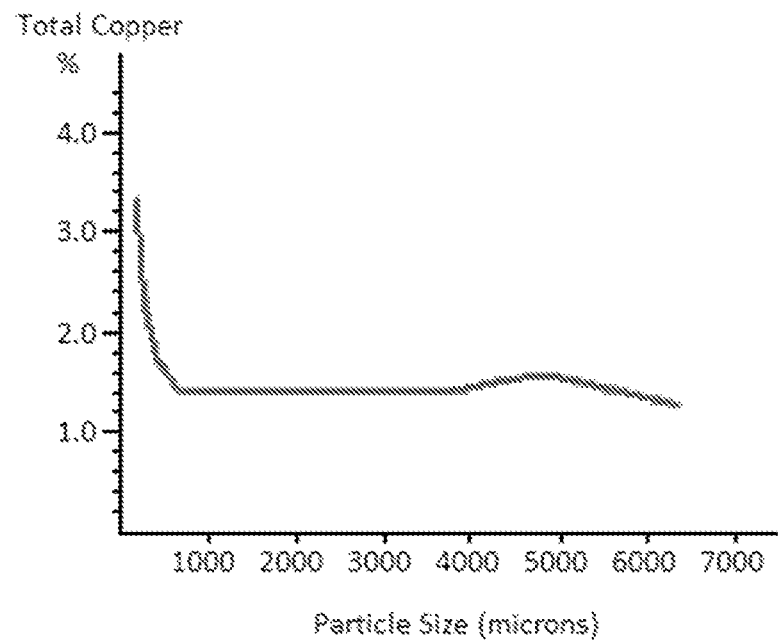
FIG. 1 shows the experimental results of measuring the amount of copper contained in particles of different size obtained from the excavation of a drilling pit.
Figure 2:
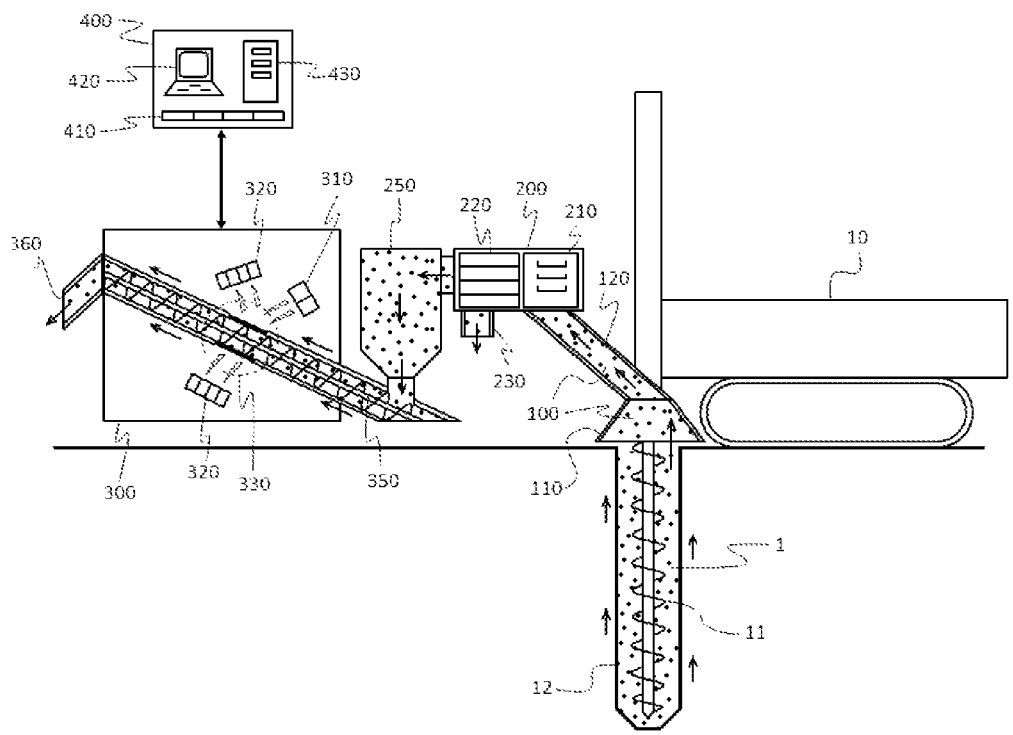
FIG. 2 schematically illustrates the best embodiment of the system and method of the present invention.
Figure 3:
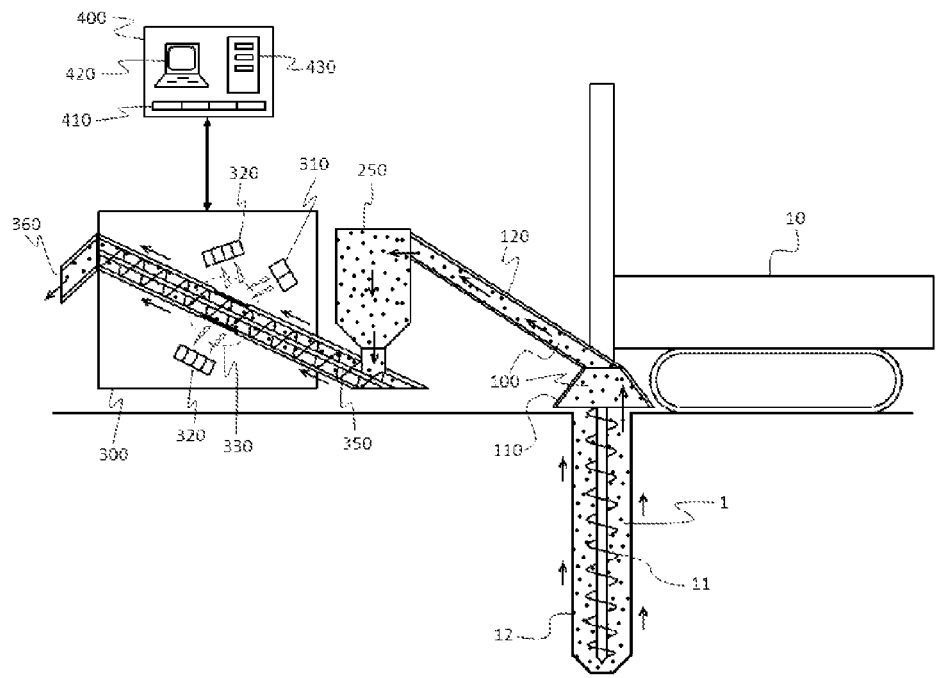
FIG. 3 schematically illustrates the system and method of the present invention with a direct connection between the collection module and the storage chamber.
Figure 4:
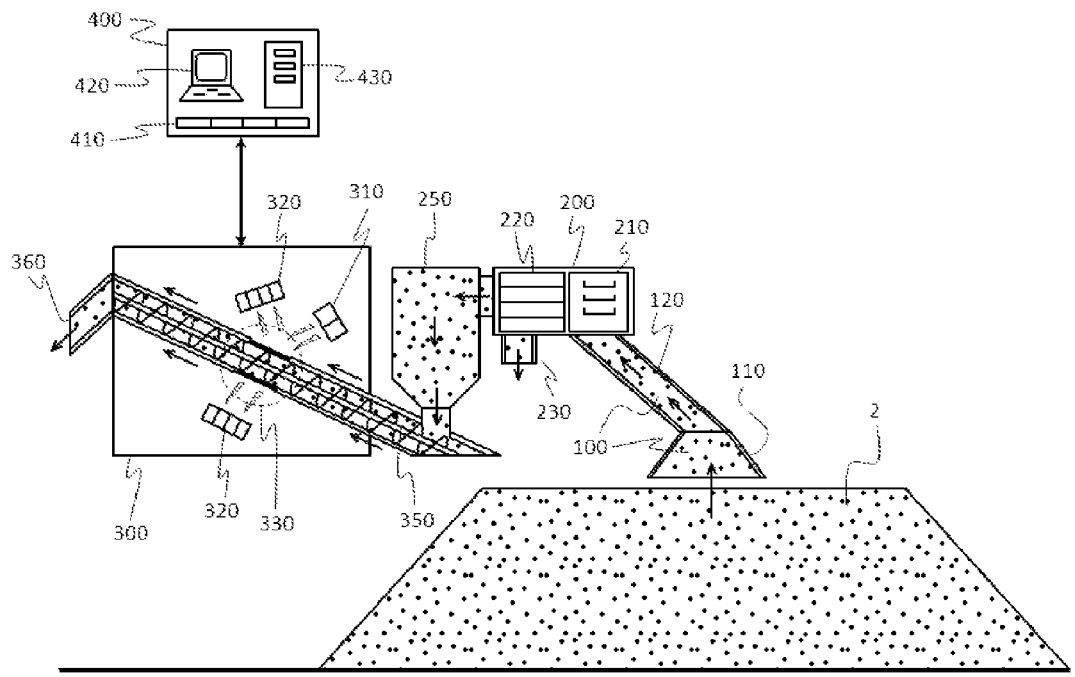
FIG. 4 schematically illustrates the best embodiment of the system and method of the present invention with debris from a stockpile.
Figure 5:
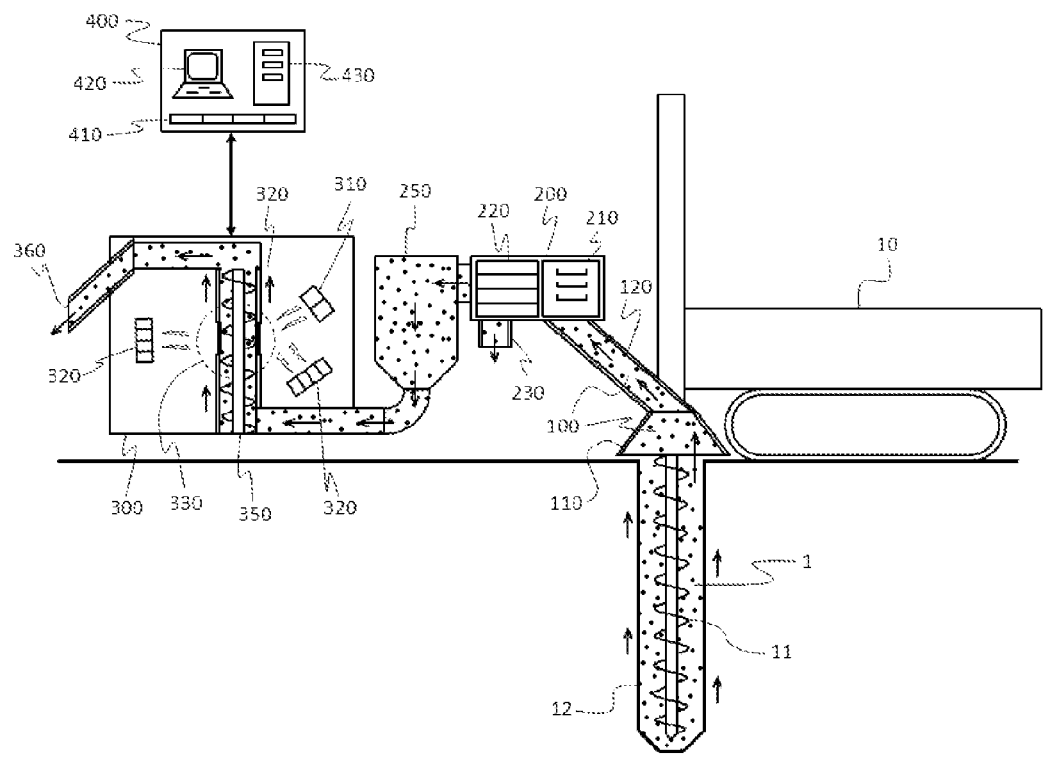
FIG. 5 schematically illustrates the system and method of the present invention with upward transportation media with right angle inclination.

According to the present invention, the real-time, non-intrusive, continuous collection, conditioning and analysis system for in situ determination of concentrations of one or more minerals in the debris (1) from a drilling pit (12), with an error of measurement less than ±2% over 10% ore grade and less than ±0.1% between 0% and 10% ore grade, consists of:

a debris collection module (100) from debris (1) comprising coupling means (110) for connecting and capture the material from the pit (11) of a drilling machine (10) excavating this pit (12), particularly capturing fine particles or dust and liquids, and debris transportation media (120) connecting to a conditioning module (200), wherein the debris (1) circulates through such debris transportation media (120), driven either by the same force that evacuates the pit or by any displacement media such as a suction pump;

a debris conditioning module (200) comprising sieving means (210), for example sieves or a sieve filter designed for passing, for example, only particles of granulometric size below 50 mm, a drying chamber (220) to remove the liquid content or moisture of the debris to a value lower than 50%, either by heating or by reducing the vapor pressure by a vacuum pump, an evacuation duct (230) to remove excess material and very coarse particles from the system, for example those with a granulometric size greater than 50 mm, and a storage chamber (250) in whose bottom the material accumulates by gravity;

one spectrum acquisition module (300) comprising upward transportation media (350) of material, for example a screw conveyor or auger, or other equivalent transportation media, which is sealingly connected to the lower portion of the storage chamber (250) and an outlet duct (360), from which the debris is released out of the system, allowing the compaction of the material by gravity and its circulation through a reading area (330), whose walls are made up of windows (340) transparent to certain electromagnetic radiation, the electromagnetic emitting means (310) including the set of photo-emitters or electromagnetic radiation sources radiating with photons the material passing through the reading area (330), and optical reading means (320) including a spectroscopic detectors or sensors (320) for detecting and measuring the photons absorbed, reemitted or diffracted by the material circulating in the reading area (330), by means of atomic or molecular spectroscopy techniques.

The debris can take the form of powder, granular material, and comminuted solids with moisture content from 0% to a slurry of 98% of moisture content. This debris can be originated in drillings being excavated at the time, from surface or depth samples from talus, tailings, open pit or underground mines, reservoirs, quarries, stockpiles, leaching piles, rubbles, it can also be originated in previous production processes or can be part of any recycling or scrap material.

a data analysis and transmission module (400) comprising data control and adaptation means (410), for example controllers and analog-digital converters, computer media (420) and communication means (430), being such data control and adaptation means (410) connected to the electromagnetic emitting means (310) and to optical reading means (320), adapting the data measured by said spectroscopic detectors or sensors (320) to digital values that can be stored in computer media (420) to be analyzed according to statistical comparison with samples of calibration material; said communication means (430) allowing transmission of stored digital values and its analysis to a remote computer media for decision making with regard to the mineral concentration of said debris.

According to yet another assembly of the present invention, real-time, non-intrusive, continuous collection, conditioning and analysis system for in situ determination of concentrations of one or more minerals in the debris (1) from a pit (12) being excavated is provided, comprising the steps of:

a) connecting coupling means (110) to a pit (11) of a drilling machine (10) and to a debris collection module (100) to capture all, or otherwise as much as possible, of debris (1) from the pit (12) being excavated, including the finer powders, the liquids and the slurries;

b) collecting the flow of debris (1) through coupling means (110), either by external drive or inner drive through a suction or vacuum pump, an air compressor or equivalent means;

c) transporting said flow of debris to a conditioning module (200) via a transportation medium (120) such as a sleeve, a pipe or hose;

d) filtering in said conditioning module (200) the flow of debris through sieving means (210), for passing, for example, only particles of granulometric size below 50 mm, by removing the larger particles and excess material through an evacuation duct (230).

e) drying in said conditioning module (200) the flow of debris into a drying chamber (220) either by heating or by reducing the vapor pressure by a vacuum pump or other equivalent drying device, reducing the liquid content or moisture of the material to a value lower than 50%, and transporting said flow of debris to a storage chamber (250), whose excess material may be removed by the evacuation duct (230);

f) transporting said flow of debris upwardly by upward transportation media (350), such as an screw conveyor or similar, to a reading area or chamber (330), in a spectrum acquisition module (300);

g) radiating said flow of debris in said reading area or chamber (330) through transparent windows (340) with electromagnetic radiation from the electromagnetic emitting means (310) consisting of one or more sources of radiation or photo-emitters arrangement; and capturing the emitted radiation that has passed through said flow of debris or the radiation that has been reemitted or diffracted by interacting with said flow of debris by optical reading means (320) consisting of spectroscopic sensors or photo-receptors using atomic or molecular spectroscopy techniques, such as x-ray fluorescence, in which case the electromagnetic emitting means (310) and optical reading means (320) operate at energy ranges between 1 and 150 keV;

h) adapting and converting to digital values the reading captured by said optical reading means (320) in an data analysis and transmission module (400) by data control and adaptation means (410), such as an analog-digital converter for its storage on computer media (420), generating a real-time value of the concentration of existing minerals of interest, and simultaneously recording the depth of the drilling machine (10) in the pit (12) being excavated and from which debris is originated, generating a continuous spectroscopic profile of the collected material in function of the depth recorded;

i) evacuating said flow of debris by a duct outlet (360) for subsequent storage, stock, containment or subsequent use in another application.

Additionally, the method of the present invention comprises the step of analyzing said digital values by suitable mathematical processing and statistical comparison with samples of calibration debris, in which the concentration of compounds is known, to obtain mineral content of elements of interest in the flow of debris. These mathematical processes allow us to estimate the concentrations of minerals of interest in validity ranges between 0 and 100% ore grade with an accuracy of ±2% over 10% ore grade and ±0.1% between 0% and 10% ore grade from photon intensities measured by optical reading means (320) and adapted by data control and adaptation means (410).

Additionally, the method of the present invention comprises the step of transmitting said digital values or mineral concentration to a remote computer media using communication means (430) to take a decision regarding to the mineral concentration of said debris.

Mode Of Carrying Out The Invention

According to another assembly of the present invention, said coupling means (110) of the debris collection module (100) can be, for example, a tight coupling, a clamp or a duct opening in the form of a bell such as to capture all the debris (1), including finer particles or dust and liquids. Meanwhile debris transportation media (120) can be, for example, a sleeve, a duct or hose, preserving all the debris captured, including finer particles or dust and liquids. For example, in an analysis of mineral concentration of debris from a drilling pit (12), said sleeve reaches the pithead (12) and coupled to a portion of the pit (11) of a drilling machine (10) that protrudes from the pit (12).

According to another assembly of the present invention, a plurality of inlet ducts is located with their openings covering most of the pithead without touching the pit (11) through which the air flow is inhaled or driven and the output of said ducts are connected to the conditioning module (200).

According to other assemblies of the present invention, said debris (1) may have another origin, such as surface or depth samples from talus, tailings, open pit or underground mines, reservoirs, quarries, stockpiles, leaching piles, rubbles, among others, as well as can be originated in previous production processes, can be part of recycling material or come of any source of interest. According to these other assemblies, the debris collection module (100) can capture the debris (1), in whole or in part, being fed either automatically or manually.

According to other assemblies of the present invention, the debris transportation media (120) of debris collection module (100) can be connected directly to the storage chamber (250) of the conditioning module (200) or can be connected directly to the upward transportation media (350) of the spectrum acquisition module (300). According to these other assemblies of the invention, the conditioning module (200) may not contain sieving means (210) or drying chamber (220) or evacuation duct (230) or collecting chamber (250).

According to other assemblies of the present invention, the conditioning module (200) may contain one or more vacuum pumps, air compressors, hydraulic pumps or other equivalent device connected to the debris transportation media (120) of the debris collection module (100) enabling driving or movement of the debris (1) for said debris transportation media (120).

According to other assemblies of the present invention, the conditioning module (200) may contain grinding media, formed, for example, by an impact mill connected to a vacuum pump, a jaw crusher, an impact crusher, a cone crusher a vertical shaft crusher according to the origin of the debris, or other equivalent grinding media for obtaining finer debris, for example, of granulometric size below 50 mm. Such grinding media are connected to the debris transportation media (120), either directly or through the sieving means (210), and either to the drying chamber (220) or the storage camera (250).

According to other assemblies of the present invention, the conditioning module (200) may contain other devices and processes that enable the debris (1) to be conditioned properly before being analyzed in the spectrum acquisition module (300), such as chemical reactors, washing processes, density separators, cooling systems, vibration damping systems, among others.

According to other assemblies of the present invention, the drying chamber (220) in the conditioning module (200) may consist of, for example, a belt filter, a vacuum filter, a pressure filter, drum filter, a disk filter, a band-pass or belt filter, a ceramic filter, a press filter, a plate filter, a hyperbaric filter, a thickener, a cyclone, a centrifuge, a microwave oven, a drying chamber by heating and cooling and or by heat exchange, or by some other equivalent means for solid-liquid separation.

In other aspects of the invention, said upward transportation media (350) in the spectrum acquisition module (300) contemplate an incident angle of 15° to 90° from the horizontal and may comprise a screw conveyor or auger, an hermetically sealed conveyor belt, a rotary helical duct, a peristaltic hose or some other equivalent means that drives debris upwardly to the reading area or chamber (330).

According to other assemblies of the invention, said electromagnetic emitting means (320) and optical reading (310) may consist of, respectively, the sources and receivers required to implement the techniques of absorption spectroscopy, fluorescence spectroscopy, fluorescence spectroscopy, X-ray spectroscopy, flame spectroscopy, emission spectroscopy, absorption or atomic fluorescence, plasma emission spectroscopy, spark or arc spectroscopy, visible spectroscopy, ultraviolet spectroscopy, infrared spectroscopy, Raman spectroscopy, mass spectroscopy, nuclear magnetic resonance spectroscopy, photoemission spectroscopy, Mössbauer spectroscopy, photoacoustic spectroscopy, photothermal spectroscopy, or other equivalent spectroscopic technique. Thus, these electromagnetic emitting means (320) can be constituted, for example, by a X-rays source, a visible light source, a gamma ray source, a microwave source, a infrared or ultraviolet light source, a magnetic source, a heat source, electrodes, a laser, a hollow cathode lamp, a photo-emitting array or some other equivalent means of emission of electromagnetic radiation. Moreover, said optical reading means (310) can be constituted, for example, by a spectrophotometer, a thermal chamber, a coil, silicon drift detector (SDD), a photomultiplier, arrays of photo-detectors and discrete sensors such as avalanche photo-diodes and photo-transistors, solid state or charge-coupled (CCD sensors) devices or other equivalent means of optical reading.

According to other assemblies of the present invention, said reading area or chamber (330) may either contain transparent windows (340) or be made of materials transparent to certain electromagnetic radiation emitted by said electromagnetic emitting means (320) and captured by said optical reading means (310).

Such means of data transmission (430) are for example a network of digital transmission via optical fiber, coaxial cable, a modem with telephone cable or wireless, radio frequency transmitters, satellite communication, etc.

According to other aspects of the present invention, the collection, preparation and analysis system can further comprise a mechanisms control module that performs the coordination and the electronic control of devices and media of the conditioning module (200) and the spectrum acquisition module (300), such as said suction or vacuum pumps, said compressors, said grinding media, said drying chamber (220), said upward transportation media (350), said electromagnetic emitting means (320), said optical reading means (310), among others; comprising a Compact RIO or PXI chassis with a protocol often used in industrial applications such as RS-485, Fieldbus or Ethernet. This mechanisms control module can perform control loops to control the flow of debris, the vacuum pressure in the debris collection module (100) or in the conditioning module (200), the intensity of electromagnetic radiation used in the spectrum acquisition module (300), among other control variables of interest to be controlled in the process.

The system and method of the present invention requires to perform a calibration prior to its field operation. This calibration allows adjustment in computing media (420), using, for example, mathematical and statistical techniques such as multiple linear regression or partial least squares regression, a prediction model of mineral content for the measurements of optical reading means (310), so as to minimize the mean squared prediction error and maximize the correlation coefficient. This calibration requires building a test set for a certain quantity of samples, for example between 50 and 200 samples, with the same characteristics of moisture, grain size distribution and mineral concentration of the debris to be analyzed during the operation, for which it was previously measured the content of the mineral of interest, for example the grade of copper or silver, using a reference method, for example, chemical analysis in a laboratory, which will validate the calibration. This calibration should be carried out periodically, for example, weekly sampling of the material being analyzed, and sent to a laboratory to be analyzed by reference methods.

As shown in the figures, the present invention is a collection, conditioning and analysis system of low error for in situ determination, in a continuous, non-intrusive manner in real-time, of the concentrations of one or more minerals of interest present in debris from drilling or other sources within the geological and mining industry or some process of extraction and processing of metals, comprising:

a) a debris collection module comprising coupling means for connecting and capturing the material as a powder, granular material, comminuted solids, from 0% moisture content to a slurry of 98% of moisture content, from a bit excavating said drill, a debris transportation media that are connected to a conditioning module, wherein the debris flows through said debris transportation media, driven either by the same force that evacuates the drilling or by a displacement medium;

b) a debris conditioning module comprising a storage chamber, in which bottom material accumulates by gravity;

c) a spectrum acquisition module comprising upward transportation media of material having an angle of incidence between 15° to 90° from the horizontal, which is sealingly connected to the lower portion of said storage chamber passing through one reading area or chamber into an outlet duct, from which the debris is released out of the system, wherein the reading area or chamber comprises some windows transparent to certain electromagnetic radiation, an electromagnetic emitting means comprising a set of photo-emitters or electromagnetic radiation sources radiating with photons to the material passing through that reading area or chamber and optical reading means including spectroscopic sensors or detectors that detect and measure the photons absorbed, reemitted or diffracted by the debris circulating through said reading area or chamber, by techniques of atomic or molecular spectroscopy; and d) an data analysis and transmission module comprising data control and adaptation means, a computer media and a communication means, being such data control and adaptation means connected to said electromagnetic emitting means and to said optical reading means.

Said debris can be originated in drillings being excavated at the time, from surface or depth samples from talus, tailings, open pit or underground mines, reservoirs, quarries, stockpiles, leaching piles, rubbles, it can also be originated in previous production processes or can be part of any recycling or scrap material.

Also in a preferred configuration, said debris conditioning module (b) further comprises an evacuation duct to remove excess material from the system, which is connected to said storage chamber of said conditioning module (b) and to said debris transportation media of said debris collection module (a), and said debris conditioning module (b) further comprises sieving means connecting to said storage chamber of said conditioning module (b), to said evacuation duct of the conditioning module (b) and to said debris transportation media of said debris collection module (a).

In another preferred configuration, said debris conditioning module (b) further comprises a drying chamber to remove the liquid or moisture content from the debris, which is connected to said storage chamber of said conditioning module (b) and to said debris transportation media of said debris collection module (a) and said debris conditioning module (b) further comprises an evacuation duct to remove excess material from the system, which is connected to said storage chamber of said conditioning module (b), to said drying chamber of said conditioning module (b) and to said debris transportation media of said debris collection module (a).

In another preferred configuration, said conditioning module (b) further comprises grinding media to obtain a finer debris of granulometric size below 50 mm, which are connected to said storage chamber of said conditioning module (b) and to said debris transportation media of said debris collection module (a), further comprising an evacuation duct for removing excess material from the system, which is connected to said storage chamber of said conditioning module (b), to said grinding media of said conditioning module (b) and to said debris transportation media of said debris collection module (a), and further comprising sieving means connecting to said drying chamber of said conditioning module (b) to said evacuation duct of said conditioning module (b) and to said debris transportation media of said debris collection module (a).

In another preferred embodiment, the debris conditioning module (b) further comprises a sieving means which are connected to said grinding media of said conditioning module (b), to said evacuation duct of said conditioning module (b) and to said debris transportation media of said debris collection module (a), and said debris conditioning module (b) further comprises grinding media to obtain a finer debris of granulometric size below 50 mm, which are connected to said drying chamber of said conditioning module (b) and to said sieving means of said conditioning module (b).

Moreover said debris conditioning module (b) further comprises grinding media to obtain a finer debris of granulometric size below 50 mm, which are connected to said drying chamber of said conditioning module (b) and to said debris transportation media of said debris collection module (a).

In another preferred configuration, said grinding media of the conditioning module (b) comprise an impact mill connected to a vacuum pump, a jaw crusher, an impact crusher, a cone crusher or vertical axis crusher.

In another preferred embodiment, said coupling means could be a tight coupling, a clamp or a duct opening in the form of a bell and said debris transportation media may consist of a sleeve, a duct or a hose.

In another preferred embodiment, said drying chamber in the conditioning module (b) reduces the moisture or liquid content to a value lower than 50% and consists of a band-pass or belt filter, a vacuum filter, a pressure filter, a drum filter, a disc filter, a ceramic filter, a press filter, a plate filter, an hyperbaric filter, a thickener, a cyclone, a centrifuge, a microwave oven, a drying chamber by heating and cooling or by heat exchange.

In another preferred configuration, said sieving means of said conditioning module (b) are sieves, a sieve filter or a sieve column for only passing particles of a granulometric size lower than 50 mm.

In another preferred configuration, said upward transportation media of the spectrum acquisition module (c) comprise a screw conveyor or auger, a hermetically sealed conveyor belt, a rotary helical duct, a peristaltic hose that drives debris upwardly to the reading area or chamber.

In another preferred embodiment, said optical reading means of the spectrum acquisition module (c) consist respectively of sources and receivers required to implement the techniques of absorption spectroscopy, fluorescence spectroscopy, fluorescence spectroscopy, X-ray spectroscopy, flame spectroscopy, emission spectroscopy, absorption or atomic fluorescence, plasma emission spectroscopy, spark or arc spectroscopy, visible spectroscopy, ultraviolet spectroscopy, infrared spectroscopy, Raman spectroscopy, mass spectroscopy, nuclear magnetic resonance spectroscopy, photoemission spectroscopy, Mössbauer spectroscopy, photoacoustic spectroscopy, photothermal spectroscopy, or other equivalent spectroscopic technique, wherein these electromagnetic emitting means consists of, for example, a X-rays source, a visible light source, a gamma ray source, a microwave source, an infrared or ultraviolet light source, a magnetic source, a heat source, electrodes, a laser, a hollow cathode lamp, a photo-emitting array; and wherein said optical reading means can be constituted, for example, by a spectrophotometer, a thermal chamber, a coil, silicon drift detector (SDD), a photomultiplier, arrays of photo-detectors and discrete sensors such as avalanche photo-diodes and phototransistors, solid state or charge-coupled (CCD sensors) devices.

In another preferred configuration, the present invention comprises a mechanisms control module that performs the coordination and electronic control of the components of the debris collection module (a), the conditioning module (b), the spectrum acquisition module (c) and the data analysis and transmission module (d).

In another preferred configuration, said displacement means of said debris collection module (a) is a suction or vacuum pump.

The present invention further comprises a collection, conditioning and analysis process of low error for the in situ determination of mineral concentrations in debris from a pit being excavated, in a continuous, non-intrusive manner in real-time, comprising the steps of:

a) collecting a flow of debris using coupling means connected to a debris collection module;
b) transporting said flow of debris from said debris collection module in a confined and upward manner by a upward transportation media having an angle of incidence between 15° to 90° from the horizontal, to a reading area or chamber in a spectrum acquisition module;
c) radiating said flow of debris in said reading area or chamber with electromagnetic radiation from electromagnetic emitting means;
d) capturing the emitted radiation that has passed through said flow of debris or the radiation that has been reemitted or diffracted by interacting with said flow of debris by optical reading means;
e) adapting and converting to digital values the measurements of said optical reading means by data control and adaptation means in an data analysis and transmission module;
f) sending said digital measurement values of said optical reading means to a computer media; and
g) evacuating said flow of debris through an outlet duct for subsequent storage, collection, containment or subsequent use in another application.

Further comprising another steps after (a) collecting said flow of debris in said debris collection module and before (b) transporting said flow of debris in a confined and upward manner by said upward transportation media to a conditioning module through a transportation media.

Further comprising a sub-step, wherein in said conditioning module such debris is sieved through a sieving means and the material of granulometric size larger than 50 mm is removed through an evacuation duct.

Further comprising a sub-step, wherein in said conditioning module the liquid or moisture content from the debris is extracted in a drying chamber to a value lower than 50%.

Further comprising a sub-step, wherein in said conditioning module said flow of debris is deposited by gravity into a storage chamber.

Further comprising a sub-step, wherein in said conditioning module the excess material is removed through an evacuation duct.

Further comprising a sub-step, wherein in said conditioning module the debris is grounded to a granulometric size below 50 mm.

Further comprising a sub-step, wherein in said conditioning module after sieving said debris the liquid or moisture content of the debris is extracted in a drying chamber to a value lower than 50% and the dried moisture is removed through an evacuation duct.

Further comprising a sub-step, wherein in said conditioning module after sieving said debris, it is grounded to a granulometric size below 50 mm.

Further comprising a sub-step, wherein in said conditioning module after grinding said debris the liquid or moisture content from the debris is removed in a drying chamber to a value lower than 50% and the dried moisture is removed through an evacuation duct.

Further comprising a sub-step, wherein in said conditioning module after sieving said debris, said flow of debris is deposited by gravity into storage chamber and the excess material is removed through an evacuation duct.

Further comprising a sub-step, wherein in said conditioning module after the liquid or moisture content of said debris is removed, said flow of debris is deposited by gravity into storage chamber and the excess material is removed through an evacuation duct.

Further comprising a sub-step, wherein in said conditioning module and after grinding said debris, said flow of debris is deposited by gravity into storage chamber.

Further comprising a further step that is prior to (a) collecting said flow of debris in said debris collection module, wherein a coupling means are connected to a bit of a drill that is in the process of excavating said pit, which capture said debris, including the fine particles or dust, the liquids and the slurries.

Further comprising another step, wherein the reading captured by said optical reading means is adapted and converted to digital values in a data analysis and transmission module by data control and adaptation means for its storage in computer media.

Further comprising another step, wherein said digital measurement values of said optical reading means are transmitted to a remote computer media.

Further comprising another step that generates a real-time value of the concentration of one or more minerals of interest present in said debris, wherein is simultaneously recorded the depth of a drill in said pit being excavated from which debris is originated, and wherein is recorded a continuous spectroscopic profile of the collected material according to the recorded depth and wherein said real-time value of concentrations of mineral of interest and said continuous spectroscopic profile are transmitted to a remote computer to take a decision regarding to the mineral concentration of said debris.

EXAMPLES

The following example illustrates but does not limit the present invention in any way.

Example 1

Figure 6:
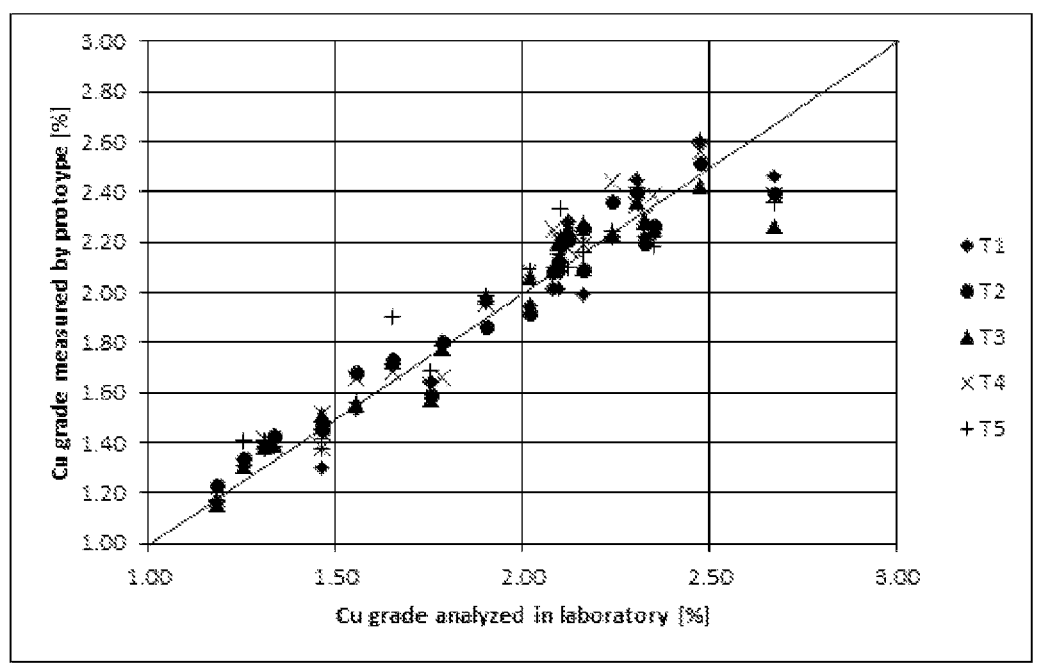
FIG. 6 shows experimental results of measuring copper grade of various powder samples of drilling pits using a prototype of the system and method of the present invention compared with the copper grade analyzed by chemical techniques in a laboratory.

In a laboratory prototype of the system and method of the present invention, the copper content was determined in various samples of dust from drilling pits in a copper mine in northern Chile. The samples were previously analyzed in a chemical laboratory. The prototype implemented X-ray fluorescence spectroscopy techniques using in the spectrum acquisition module an X-ray tube with a target of silver and an emission spectrum of 3 to 40 keV range as electromagnetic emitting means and a silicon drift detector (SDD) with an optimal energy range from 1 to 40 keV as optical reading means. Dust samples analyzed had a copper grade between 1% and 3% according to chemical analysis and were finely grounded and their moisture content did not exceed 3%. Samples were located inside a box which was moved upwardly using an angle of incidence of approximately 30° from the horizontal, passed under the X-ray tube and the detector in a closed reading chamber. Five readings were taken for each sample. The results of the measurements are illustrated in FIG. 6, having obtained for samples assayed an average relative error of 3.8% and a maximum relative error of 11.1% (having averaged the five readings of each sample) relative to the copper grade tested in laboratory.

The various embodiments of the invention described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the following claims.

We claim:

1. A collection, preparation and analysis system of low error for in situ determination, in a continuous, non-intrusive manner and in real-time, of the concentrations of one or more minerals of interest present in debris from drilling or other sources within geological and mining industry or from any process of extraction and processing of metals, comprising:
   a) a debris collection module comprising coupling means for connecting and capture the material as a powder, granular material, comminuted solids, from 0% moisture content to a slurry of 98% of moisture content, from a bit excavating said drilling, a debris transportation media that are connected to a conditioning module, wherein the debris flowing through said debris transportation media is driven either by the same force that evacuates the drilling or by a displacement media;
   b) debris conditioning module comprising a storage chamber, in which bottom material accumulates by gravity;
   c) a spectrum acquisition module comprising upward transportation media of material having an angle of incidence between 15° to 90° from the horizontal, which is sealingly connected to the lower portion of said storage chamber passing through one reading area or chamber into an outlet duct, from which the debris is released out of the system, wherein the reading area or chamber comprises some windows transparent to certain electromagnetic radiation, an electromagnetic emitting means comprising a set of photo-emitters or electromagnetic radiation sources radiating with photons the material passing through that reading area or chamber and optical reading means including spectroscopic sensors or detectors that detect and measure the photons absorbed, reemitted or diffracted by the debris circulating through said reading area or chamber, by techniques of atomic or molecular spectroscopy; and
   d) a data analysis and transmission module comprising data control and adaptation means, a computer media and a communication means, being such data control and adaptation means connected to said electromagnetic emitting means and to said optical reading means.

2. The system according to claim 1, wherein said debris conditioning module (b) further comprises an evacuation duct to remove excess material from the system, which is connected to said storage chamber of said conditioning module (b) and to said debris transportation media of said debris collection module (a).

3. The system according to claim 2, wherein said debris conditioning module (b) further comprises a sieving means which are connected to said storage chamber of said conditioning module (b), to said evacuation duct of said conditioning module (b) and to such debris transportation media of said debris collection module (a).

4. The system according to claim 1, wherein said debris conditioning module (b) further comprises a drying chamber to remove the liquid or moisture content from the debris, which is connected to said storage chamber of said debris conditioning module (b) and to said debris transportation media of said debris collection module (a).

5. The system according to claim 1, wherein said conditioning module (b) further comprises grinding media to obtain a finer debris of granulometric size below 50 mm, which are connected to said storage chamber of said conditioning module (b) and to said debris transportation media of said debris collection module (a).

6. The system according to claim 4, wherein said debris conditioning module (b) further comprises an evacuation duct to remove excess material from the system, which is connected to said storage chamber of said conditioning module (b), to said drying chamber of said conditioning module (b) and to said debris transportation media of said debris collection module (a).

7. The system according to claim 5, wherein said debris conditioning module (b) further comprises an evacuation duct to remove excess material from the system, which is connected to said storage chamber of said conditioning module (b), to said grinding media of said conditioning module (b) and to said debris transportation media of said debris collection module (a).

8. The system according to claim 6, wherein said debris conditioning module (b) further comprises a sieving means which are connected to said drying chamber of said conditioning module (b), to said evacuation duct of said conditioning module (b) and to said debris transportation media of said debris collection module (a).

9. The system according to claim 7, wherein said debris conditioning module (b) further comprises a sieving means which are connected to said grinding media of said conditioning module (b), to said evacuation duct of said conditioning module (b) and to said debris transportation media of said debris collection module (a).

10. The system according to claim 4, wherein said debris conditioning module (b) further comprises grinding media to obtain a finer debris of granulometric size below 50 mm, which is connected to said drying chamber of said conditioning module (b) and to said debris transportation media of said debris collection module (a).

11. The system according to claim 8, wherein said debris conditioning module (b) further comprises grinding media to obtain a finer debris of granulometric size below 50 mm, which is connected to said drying chamber of said conditioning module (b) and to said sieving means of said conditioning module (b).

12. The system according to claim 5, wherein said grinding media of said conditioning module (b) comprising an impact mill connected to a vacuum pump, a jaw crusher, an impact crusher, a cone crusher or a vertical axe crusher.

13. The system according to claim 1, wherein said debris is originated in drillings being excavated at the time, from surface or depth samples from talus, tailings, open pit or underground mines, reservoirs, quarries, stockpiles, leaching piles, nibbles, it can also be originated in previous production processes or can be part of any recycling or scrap material.

14. The system according to claim 1, wherein in the debris collection module (a) said coupling means can be a tight coupling, a clamp or a duct opening in the form of a bell and said debris transportation media can consist of a sleeve, a duct or a hose.

15. The system according to claim 4, wherein said drying chamber in the conditioning module (b) reduces liquid or moisture content to a value lower than 50% and consists of a band-pass or belt filter, a vacuum filter, a pressure filter, a drum filter, a disc filter, a ceramic filter, a press filter, a plate filter, an hyperbaric filter, a thickener, a cyclone, a centrifuge, a microwave oven, a drying chamber by heating and cooling or by heat exchange.

16. The system according to claim 3, wherein said sieving means of said conditioning module (b) are sieves, a sieve filter or a sieve column for passing only particles of granulometric size below 50 mm.

17. The system according to claim 1, wherein said upward transportation media of the spectrum acquisition module (c) comprise a screw conveyor or auger, a hermetically sealed conveyor belt, a rotary helical duct, a peristaltic hose that drives debris upwardly into the reading area or chamber.

18. The system according to claim 1, wherein said electromagnetic source means and said optical reading means of the spectrum acquisition module (c) consist respectively of sources and receivers required to implement the techniques of absorption spectroscopy, fluorescence spectroscopy, fluorescence spectroscopy, X-ray spectroscopy, flame spectroscopy, emission spectroscopy, absorption or atomic fluorescence, plasma emission spectroscopy, spark or arc spectroscopy, visible spectroscopy, ultraviolet spectroscopy, infrared spectroscopy, Raman spectroscopy, mass spectroscopy, nuclear magnetic resonance spectroscopy, photoemission spectroscopy, Mossbauer spectroscopy, photoacoustic spectroscopy, photothermal spectroscopy, or other equivalent spectroscopic technique, wherein these electromagnetic emitting means consists of, for example, a X-rays source, a visible light source, a gamma ray source, a microwave source, an infrared or ultraviolet light source, a magnetic source, a heat source, electrodes, a laser, a hollow cathode lamp, a photo-emitting array; and wherein said optical reading means can be constituted, for example, by a spectrophotometer, a thermal chamber, a coil, silicon drift detector (SDD), a photomultiplier, arrays of photo-detectors and discrete sensors such as avalanche photo-diodes and photo-transistors, solid state or charge-coupled (CCD sensors) devices.

19. The system according to claim 1, wherein the system comprises a mechanisms control module that performs the coordination and electronic control of the components of the debris collection module (a), the conditioning module (b), the spectrum acquisition module (c) and the data analysis and transmission module (d).

20. The system according to claim 1, wherein said displacement means of the debris collection module (a) is a suction or vacuum pump.

21. A collection, preparation and analysis process of low error for in situ determination of mineral concentrations in debris, in a continuous, non-intrusive manner in real-time, comprising the steps of:
  a) collecting a flow of debris using coupling means connected to a debris collection module as a powder, granular material, comminuted solids, from 0% moisture content to a slurry of 98% of moisture content;
  b) transporting said flow of debris from said debris collection module in a confined and upward manner by a upward transportation media considering an angle of incidence between 15° to 90° from the horizontal, through a reading area or chamber in a spectrum acquisition module;
  c) radiating said flow of debris in said reading area or chamber with electromagnetic radiation from electromagnetic emitting means;

d) capturing the emitted radiation that has passed through said flow of debris or the radiation that has been reemitted or diffracted by interacting with said flow of debris by optical reading means;

e) adapting and converting to digital values the measurements made by optical reading means by data control and adaptation means in an data analysis and transmission module;

f) sending said digital measurement values of said optical reading means to a computer media; and g) evacuating said flow of debris through an outlet duct for subsequent storage, collection, containment or subsequent use in another application.

22. A process according to claim 21, wherein said flow of debris is transported to a conditioning module by a transporting media, after (a) collecting said flow of debris in said debris collection module and before (b) transporting said flow of debris in a confined and upward manner by said upward transportation media.

23. A process according to claim 22, wherein said conditioning module said debris is sieved through a sieving means and the material of granulometric size greater than 50 mm is removed through an evacuation duct.

24. A process according to claim 22, wherein the liquid or moisture content of the debris is extracted in a drying chamber to a value lower than 50%, in said conditioning module.

25. A process according to claim 22, wherein said conditioning module said flow of debris is deposited by gravity into a storage chamber.

26. A process according to claim 25, wherein the excess material is removed through an evacuation duct in said conditioning module.

27. A process according to claim 22, wherein the debris is grounded to a granulometric size below 50 mm in said conditioning module.

28. A process according to claim 23, wherein after sieving said debris, the liquid or moisture content of the debris is extracted in a drying chamber to a value lower than 50% and the dried moisture is removed through an evacuation duct in said conditioning module.

29. A process according to claim 23, wherein after sieving said debris, the debris is grounded to a granulometric size below 50 mm in said conditioning module.

30. A process according to claim 29, wherein after grinding said debris, the liquid or moisture content of the debris is extracted in a drying chamber to a value lower than 50% and the dried moisture is removed through an evacuation duct in said conditioning module.

31. A process according to claim 23, wherein after sieving said debris, said flow of debris is deposited by gravity into a storage chamber and the excess material is removed through an evacuation duct in said conditioning module.

32. A process according to claim 24, wherein after removing the liquid or moisture content of said debris, said flow of debris is deposited by gravity into a storage chamber in said conditioning module.

33. A process according to claim 28, wherein after removing the liquid or moisture content of said debris, said flow of debris is deposited by gravity into a storage chamber and the excess material is removed through an evacuation duct in said conditioning module.

34. A process according to claim 27, wherein after grinding said debris, said flow of debris is deposited by gravity into a storage chamber in said conditioning module.

35. The process according to claim 21, wherein before (a) collecting said flow of debris a coupling means are connected to a bit of a drill that is in the process of excavating said pit, which capture said debris, including the fine particles or dust, the liquids and the slurries.

36. The process according to claim 21, wherein the reading captured by said optical reading means is adapted and converted to digital values in a data analysis and transmission module by data control and adaptation means for its storage in computer media.

37. The process according to claim 21, wherein additionally comprising the step of transmitting said digital values of the measurements of said optical reading means to a remote computer media.

38. The process according to claim 21, wherein a concentration value of one or more minerals of interest present in said debris is generated in real-time, simultaneously recording the depth of the drilling machine in the pit being excavated and from which said debris is originated, and a continuous spectroscopic profile of the collected material in function of the depth recorded is obtained.

39. The process according to claim 38, wherein transmitting to a remote computer media said real-time value of concentrations of mineral of interest and said continuous spectroscopic profile to take a decision regarding to the mineral concentration of said debris.

* * * * *